(12) United States Patent
Schmidt et al.

(10) Patent No.: US 6,503,748 B2
(45) Date of Patent: Jan. 7, 2003

(54) ENDOGENOUS KETOGULONIGENIUM PLASMID

(75) Inventors: Thomas M. Schmidt, East Lansing, MI (US); Steven F. Stoddard, Decatur, IL (US)

(73) Assignees: Archer-Daniels-Midland Company, Decatur, IL (US); Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 09/826,205

(22) Filed: Apr. 5, 2001

(65) Prior Publication Data

US 2002/0064871 A1 May 30, 2002

Related U.S. Application Data

(60) Provisional application No. 60/194,625, filed on Apr. 5, 2000.

(51) Int. Cl.$^7$ .......................... C12N 15/63; C12N 1/21; C07H 21/04
(52) U.S. Cl. ................ 435/252.3; 435/320.1; 536/23.1; 536/24.1
(58) Field of Search .............. 536/23.1, 24.1; 435/320.1, 252.3

(56) References Cited

U.S. PATENT DOCUMENTS

| | | | |
|---|---|---|---|
| 4,933,289 A | 6/1990 | Imai et al. | 435/253.3 |
| 4,935,359 A | 6/1990 | Yin et al. | 435/138 |
| 5,399,496 A | 3/1995 | Fujiwara et al. | 435/69.1 |
| 5,474,924 A | 12/1995 | Nogami et al. | 435/138 |
| 5,580,782 A | 12/1996 | Beppu et al. | 435/252.1 |
| 5,834,231 A | 11/1998 | Stoddard et al. | 435/42 |
| 5,989,891 A | 11/1999 | Liaw et al. | 435/244 |
| 6,316,231 B1 | 11/2001 | Stoddard et al. | 435/138 |
| 6,319,699 B1 | 11/2001 | Stoddard et al. | 435/138 |

FOREIGN PATENT DOCUMENTS

EP   1 076 094 A2   2/2001

OTHER PUBLICATIONS

Urbance, J.W. et al., "Taxonomic characterization of *Ketogulonigenium vulgare* gen. nov., sp. nov. and *Ketogulonigenium robustum* sp. nov., which oxidize L–sorbose to 2–keto–L–gulonic acid," *Int. J. Systematic Evol. Microbiol.* 51 :1059–1070, Society for General Microbiology (May 2001).

Vandamme, E.J., "Production of Vitamins, Coenzymes and Related Biochemicals by Biotechnological Processes," *J. Chem. Tech. Biotechnol.* 53:313–327, Elsevier Applied Science (1992).

Claim as pending Apr. 9, 2002 in U.S. patent application No. 09/684,970, Stoddard et al., as filed Oct. 10, 2000; a divisional of U.S. application No. 09/290,234, now U.S. patent No. 6,319,699 (document AI1).

Claims as pending Apr. 9, 2002 in U.S. patent application No. 09/722320, Stoddard et al., filed Nov. 28, 2000: a divisional of U.S. patent application No. 09/393,655, now U.S. patent 6,316,231 (document AH1).

Claims as pending Apr. 9, 2002 in U.S. patent application No. 09/722,514, Stoddard et al., filed Nov. 28, 2000: a divisional of U.S. patent application No. 09/393,655, now U.S. patent 6,316,231 (document AH1).

Claims as pending Apr. 9, 2002 in U.S. patent application No. 09/722,427, Stoddard et al., filed Nov. 28, 2000: a divisional of U.S. patent application No. 09/393,655, now US patent 6,316,231 (document AH1).

U.S. patent application No. 09/826,206, D'Elia, J., filed Apr. 5, 2001.

U.S. patent application No. 09/826,191 (pending), D'Elia, J. et al., filed Apr. 5, 2001.

Delic, V., et al., "Microbial Reactions for the Synthesis of Vitamin C (L–Ascorbic Acid)," in *Biotechnology of Vitamins, Pigments and Growth Factors*, Vandamme, E.J., ed., Elsevier Applied Science (London & New York) pp. 299–336 (1989).

Sugisawa, H., et al., "Microbial Production of 2–Keto–L–Gulonic Acid from L–Sorbose and D–Sorbitol by *Gluconobacter melanogenus*," *Agric Biol. Chem.* 54:1201–1209, Japan Society for Bioscience, Biotechnology, and Agrochemistry (1990).

*Primary Examiner*—Remy Yucel
*Assistant Examiner*—Katharine F Davis
(74) *Attorney, Agent, or Firm*—Sterne, Kessler, Goldstein & Fox P.L.L.C.

(57) ABSTRACT

The present invention relates, in general, to an isolated or purified nucleic acid molecule comprising a nucleotide sequence of an endogenous plasmid contained in NRRL Deposit No. B-30035.

25 Claims, 5 Drawing Sheets

SEQ ID NO:1

```
   1 TGGTGAACGC ATTGGCTTGA TGTTTGAGAA AAGCGAAAAG ACCCGGCCAC
  51 AGTTGTGGGT AGAGCGTCGA TATGTGCAAG ACCTGATGCT TGCTGACATC
 101 GAACTCCGTG TCTACCTCGC ATCGTCGCTG TATCAGCCTG CTGCGGATGG
 151 CGGAAAGCCC GCCTATGGTC GTCACGCAGC CCTTAAGGCG ATGCGCGACT
 201 TGGCCCATGC CGATCTGGTG CGTTTCACCA TCGGCCGGAT TACGCAACTG
 251 GAGATGATCC TAGAGCGGTT AACCGAGACA TCTGGTTAAC GCCATAAAGG
 301 CTGCGGCATG AAAATAGGCG GACAATCTGC GCTTGGCCGC CCCCGTTCTC
 351 AGCCGTGCTT GCTCTCTGCC TGCATGGCAC GACGCAGGAT CGCGTTCATA
 401 CGGGTCTGAT ATCCAGACCC GCCCGCCTTG AGCCATGCCA GCACATCGGC
 451 ATCAAGCCGC GCGGTGATCT GCTGCTTGAT CGGGCGATAG AAGCGCCCAC
 501 GCTCGGCGTC TGCCCATTGG GCTTCGGTCA GCTCGGGAAC ATCGTTGGTG
 551 TCGATCTGCT CGGGCGGCAG AGCGTCCAGC CGCGCCAATT TCTTGCGGCG
 601 CTCCTCGGTA AGAGCGGGCA GCGTATCGAA GGTGTATTCA ACCATTGGCA
 651 TATCTCTTCC TTTCCTGCGG TGTAGCGCGG CGAGCCGAAA TGATGCGGAT
 701 CGTCTCGACC GGATCGGGGC CAGCCTCGAT GATCAGGTGG GCAACCAGAA
 751 GGACGGCAGC GCCATAGATC TGCCCAACGG TTTGCCAGCG GTATTCCCCG
 801 CCCTCGATCC TATCCTGAAC CGTCAGGTGC AACGGATCGG CGAACACATG
 851 CACAGCATCC TCGAACCGGA TGCCATGCTT CTTTTCGTTC GTTTCCGCCT
 901 TGGCGGGATC CCAGATAAAC CGCATCTTCA TGGCAGAATT ATAACTACAC
 951 ATTTGTAGTT ATTCAATGCC AAGTCGCAGG TTCAAATCAC GCCCCCAAAC
1001 CGCAACTGTA TTCGTTCTAC TCACGCGCGC TTTTGAATAG AAGCTTGCAT
1051 GATAACACCC GCCGCGTCCT CAACAAAATA AGGCAAATCC GCCGCGCTGG
1101 CGCAATCTGC GCTTTGTCGA TGCAAGGTCT TGTGGTTTCA TACTGCAAGA
1151 GCATGCAAGG AATTGCCCCG GATGAGCACC ACGACGACAC CCACCAAGCC
1201 GGCCTGGAAC AAGGGCCGCG TTGTCGGGAA AAAGCCGCCG CTGACACCTG
1251 ACCAGATTGC CCTGATCCGT CTCATCCTGC GCCAGGAACG GGCGTGGCGG
1301 GATCTGGCTC TGTTCAACGT GGCGATCGAC ACCAGTTTGC GCGGCTCGGA
1351 CCTCGTGCGC CTGCGCGTCT CGGATGTGGC GACCCCAGCT GGTCTGCGTG
1401 AGATCGTCGA GATCCGCCAG AAGAAGACCG AGGCCCGCAA TGTCCGCCCC
1451 GTACAGGCCC GCCTGTCGGA GGGGACACGC GAGAGCCTGC GGGTCTATCT
1501 CGCGGCCTCT GACAAGCCGC TGCACAGCTG GCTGTTCACC GGACAGGGCA
1551 TCCGCTGGTC CCACACCCAC CTTAGCGAGA GCCAGCTGTG GCGCCTGTTC
1601 AAGTCCTGGC TCGAGAAGGC GCGGCTCGAT CCCAGCCTCT ACGGGCTGCA
1651 CTCGCTGCGC CGAACCTTCC CCAGCCACAT CTACCGCGAG ACCGGCAATC
1701 TGCGCGCCGC ACAGCTGCTG CTGGGCCATG CCAGCATCGA GAGCACCAAG
1751 GAGTACATCG GCACCGAGCA AGCCGAGGCC CTCGATATCG CACGGAGGTA
1801 TCACCTCTAA CCCATGGAGA CCTATCTCGA GAAGCGCATC CCCGCCAAGA
1851 ACACAGCACG GTTCTACCGC ATGGCGGTCC TGCCGAACCT GTTCGGGGAA
1901 TGGACGCTGT ATCGAGAATG GGGCCGCATT GGCATCAGCG GCCGCATCCG
1951 GCTCGATTGG TTTGAGAGTG AACAAGATGC CATCGCTGCG ATGCTCGCCA
```

FIGURE 1A

```
2001  TCGAGACCGC CAAGCGTCAG CGCGGGTATT GGCTCGAGCC CATCCAGATT
2051  GACATGTTCC CAGGGGCATA ACAGGCCATC AATGTAAGAG TGCAAGCGGA
2101  GCAAGCAAAA GCCATTTCAC AGTGAGGTGG CAGATGTTCC TGTTTCACAG
2151  TGAAAGCGCT GATGCTGTTT CCACGCCACA GACTGATACG ACCAAAGCAA
2201  CGGGGTCTGC CGCCACAGAC CGGTTCGCCG GCCACCCGCA GAAACGCAGG
2251  TAAAATGGCG ATTTCCGCAA AAAACCGTG CAAATGATGG CAAATCACCA
2301  TCCAGTTTCA TCCTGAAACC CGTCGCTCAA CATGAACGAG CAGGCCATCA
2351  TCCAAGCCCC AGAAACGCGG TGCGGCGACT ACAGATGAGC GATGTTCTGG
2401  CTCATAGGCT GCAAGGCCCT GCAACAGTGA TTTCACCGTG AGATTGCAGG
2451  GTCTTTTGGC TCTCCCGCAA GAGCCACCTC AGGGTGAGCG AGCTAGCCGT
2501  CTAGGTTCAC AGTGAAATCG CTGAGGAGCG TTGCGGGGCT TATGGTTTGG
2551  CTGGTCACGT TGGCCATCGG AATGGAGCAT ACGATGGCTT CTACGCAGTC
2601  GAATCCTGAG GCTTCACGTG GGAAAAATAC GCTCCAAAAA AGCCCTGACC
2651  AAATCTTGGA AAAATTGCTT GAAAAGTTTG CTTCTAAAAA ACTGGGAACG
2701  AGATATGCAC GAGATCCCTT ACGAGTGCTG TAGGAGTAAT GCAGTGGACA
2751  AAAACGCCAT TTTTTGCCCC AGTAGGAGTA ATGGAGTGGT TATTTTTTGG
2801  GAGATTTTGC TTCAGTAGGA GTAACGCGTT GGTTAAATTT GCTTGATTGG
2851  CGGTTCAAAT CGACCACCGA GCTGCCGTTG GTCGTATTCG ATCTGCCCCG
2901  CAATTGGGCA CTTGCAGGCC ATCCCCTGA ACTTCTGGCG ATGACCATTT
2951  CGAAGGCAAT GGGTCGAAAT TCATAGAATT TTGTGTGAGG TGCGTAGCGG
3001  CTCTGACAGG GGTGCTGCGC GGAGATCTCT GGTCTCAGGT AGGGCGACAA
3051  TGGAGAGGTG TTAGTTGCCC CCTGTATCGC TCTCTGCGTG GCGCATTGGG
3101  TCATCCTGCC CGGACATATG ATATTCCGCT AGAGGATTAC TGATAGTTTC
3151  TGCCTGTCGG GCTTGTCGGG CTTGTCGGGC TTGTCGGGCT TGTCGGGCCT
3201  GTCCCTCTTG TCCCGCCTGT CCTCACTTTT TCACAATCAA AAAATGGGCG
3251  AAGCCCTTCT TGTTCTATAG TTCTTATAGT TCATACGAAA ATTACACATA
3301  ATTATCAATA GCTTATTCGC TTAAAAGGGA GTAATTGGGC CGCAAAAGGG
3351  AGTAATTGGG CCGCAAAAGG GAGTAATTGG GCCGCAAAAG GGAGTAATTG
3401  GGCCGATATC GGTTGTTTAC ATGGGGAGGA ATCCCCTTAA TCATTTCTCC
3451  CCATGGGAAA GACAACACAA GTGGCCGCAG ACCGGGCCTT CGACCAGACA
3501  AAAACTGTGC TCCCTGCCGA GGTGGCGAGA GGGGTCTATA TGCGCAATCC
3551  GCCCCGCCTG CAGGCGCTCA AGCTCATGCA TTTAATGATA GCCACTGCGG
3601  GCGGCCGCAT GGCTGATGAT GTGCGCCATG AAATGCGGCT GGCCGACATT
3651  CGCGCAATCG ACGGCATGAA AACCATGAC CGTGAGAGCC TGACCCCGCT
3701  GTTCGAGGAG CTAGCCGCTG CGGTGTTGAC CCATGATGAC CCTGCAAAGA
3751  TGATCGTGAC AGTCGGCGGC TTGGTCGATG AGGCGCGAAT AGACTACCGC
3801  CAGGAGGCAA GCGGCGAACT CCTAGTGACG TGGACCTTCC GGAGTACATT
3851  CCGTCGTATG GCGGCGGAGT CGAACCACTG GCCATTCTC GACCGTCAAA
3901  CGGTATTCCA TCTCGGTAGT AAGTATTCCG TGCTGCTGTT CCAGCACGTC
3951  TCTAGTCTCG CCAATCTTGA TCGGATGAGC GCGAAAACCT TTACGGTCCC
4001  CGAGTTGCGG GCGCTCCTTG GAGTGCCCGA GGGAAAGATG GTTCGTTGGA
4051  ACGACGTTAA CAGATTTGCT CTCAAACCTG CACTGGATGA GATCAACCAT
```

FIGURE 1B

```
4101  TTATCGCGTC TGACATTGAC GGCAAAGCCG ACCAAGATTG GCCGTAGCGT
4151  GGCAAGTGTG ACTATAGGCT GGGAAGTGAA AGACGACCCA ACCGTCGCCA
4201  GGCGCGAGCT GGCGGGTTCC AAGGTCGGTC GAGATGCTCG TCGCAGAGGG
4251  GCAGCGGAAA CGATAGCCCC CTCCTTCCCA GAAGCGGGCG GGATCACCTA
4301  CAGTCCACGT TGGCTGGAGC TGAAACGCTC TGCTGGCAGC AACAAGGACA
4351  ACGATCTGAT CGCCTCAGAC TTCCGGCGTT TCTGTCGGGA GAGAGGCGTG
4401  CGTCTGGACG CTGCAAACAT CGAAAAACTG TTTTTAGATT TCTGCGCAAA
4451  GGTAGGGAAG GTTTGAGTTT TGAGGTATTT CACCGCAATA GTGTTAAATG
4501  ACTTTCGTGA AACGATGTGC AATATAGCGG TAAGACTATG AAATACACGG
4551  CTGGACAGGC TGCAAAAGCA ACGGGTGTGG CGACCGCAAC CATCACTCGG
4601  GCGCTAAAAA GCGGTAAAAT TTCCGGTAAA AAGATGAAT CTGGGGCATG
4651  GGTTATAGAT CCTGCAGAAT TGCACAGAGT GTTTCCTCCC ATTTCAAAGA
4701  AATACACCGA ACACCTAAC ACGCAAGTAT ATGGTAAGCG TGATGAAACA
4751  CATGAAATGA CCTCAGAAAT CAGCGCATTA GAGCGTGAAG TTCGGACTTT
4801  ACGCGATGCT TTATCTGATG CCAGGGAGGA TCGCGACAAA TGGCGCGACA
4851  TGGCCGAGCG TCTTTCAATT TCATCACCGA TGAGAGAGGA AGACCGCCCC
4901  CCTCAAAAAC AAAGATGGTG AAGATATTC TGATCCTGGG CTTCAGGAGC
4951  CTTGCCTTTA AAACCTGAAT CAGCATTCTA GCGATGCTGA TAAGAAGTAA
5001  ATATAGCCAC AATAGAGCGG CCATTTTCCA TTCACATACA GCTCATCATG
5051  TGATCAATAT CAAGTATTGA TATTCATCAA TGGAGAAGAA TTTACATGTA
5101  TCACAGGATC ATCACAGCAT TTGTTTTGT ATTTCTAAGT GCTAACATAA
5151  CTATCGCTGG CCCTAAAGAA GATTGTACTA TTGCAGTATC TCACCTTGGG
5201  TTTCAGACCG ATAATTACAG CTTTGTCGAA GCCGGTTTTT TTGCCAGAGA
5251  GAGACACGTT TTTGATGGTG TAATAAACTG CTACGTATCT CATGATGGTA
5301  ACATACACAG CATCATCCGG GGCAACACAC CTCTTATGGA AGATGGATAT
5351  TATGGCCCAG AAGTACTGGC GGAAAAACGC GATATTGAGG CACAGGCCCG
5401  CACTTTAGAG GCGGAAGCCT ATAACGAGTA CCAAAACACT AGAAGCCAGA
5451  TTGAGGAAAA TAGGGAACGT GCCCTCGAGG CGCTGCGGCT AGCTAGCAGT
5501  CCTTTTATTA ATAATGGTAG TACAGAAGAA CAGACAATTA TACAGGCCGC
5551  AACTCCGACG GCAGATCCTG TTGTATCTGT ACCCGTGGCA CTCCAGAAT
5601  CTAAACAAAG TCGAGAGCCG GAACCGGCTG CTGTTCCAGC ATCAGTTTCT
5651  GTTAGAGAGA TGTGGAGCAC GGCTGACAGA TTGACCACCC GTACATGCCC
5701  ATCGACTCGA TGCGGAGCAA CTAGCTGGGT AACAGATGGA ACTAAAGTAA
5751  CAGTTTATGA AGAAAAGAC GGTTGGTCTA GAATCGGAGA GCTACAGTCT
5801  GCAATGTGCA TAAATGGAAT AAGTGGCGCG GTCGATTCAG GTGAATCTTC
5851  CTGCAATCCC ACCAATGGTA TCGTTAATGG GCAATTCGCA CCCTGGGTTT
5901  TCTCGGATTA TCTTACGATC CAAGAGCCAG AAGCTCCCAT ATCCACCCAA
5951  GAGTGTCGAA ATATGGGGCT CGAGAACTCA GATAATTACC GTATCTATTC
6001  TAGTCAGTTC TGCACTGCCG CTCTCGAAAT GATCAACGAT AGAGTATGCA
6051  ATACATCTGA TTTCAGAGAT TTAGCTTGGT TATCTTCTCC TGAAAGAGGA
6101  CAGGATTACT ACTTCACCTA TTGTGGCGGA TTTCAACCTC AAAACAGATG
6151  GTATTTGAAT GTCAGGACAG GTGAAATCAC CCGCTGATAT TCCACCAAGG
```

FIGURE 1C

```
6201 TGAGTCCTGT AGATCAGACT CTCAAGGAGT AAACGTTTTA ATCCATCTCC
6251 ATGAGATCAA CATAGATAGG TGTTCAGTCC CGGCATCTGG TGGATCGGGT
6301 TTAGGATGAA TCTGTCCGGC TCTTGACATA CCCCCGCGTG AAACCCTGTC
6351 TTTACAAGAG AAAGTCAGCG GCCTCGAAGC CGCTCTAGCC GATGCCCGGG
6401 CCCAACGGGA TGAGTAGAGC GAACAAGCAA AGCGCCTAGC TATGGCTCTG
6451 CCCGTCCCGG AAGCTGCAGC CGCAGAATCC GGAAAAAAGA AAAATACAT
6501 GGCAGCGATT ATTTGGATAG GACACAATCC TTTTCTATTA ATATACAACA
6551 AGATATGGGC ATGCGCCGCG CGTGATCCTC ATTCGATACA ATCCAAATCC
6601 TGAAAGCTGA CTATGCCCTA CGCATCGCGC ACCATCGGTG CCGTCATTGA
6651 TGACGTGAAC CGCACCTACC TGCTGCCCGC AATCCAACGC CCCTATGTCT
6701 GGTCTGCCGG ACAGGTCGTT GCGCTGTTCG ACTCTCTGTT GAAGGGCTAT
6751 CCGATCAGCA GCTTCATGTT CTGGGCGGTG GACGAGGAGA CCAAGGCAGA
6801 GCTGCGATGC TACAAATTCA TCGAGAATTA TCGGCCCGAA ATGATGAACG
6851 AGCCGACTAG TGCGGACGGG CGGCAGGTCG TCCTTGTGCT CGACGGACAG
6901 CAGCGGATGA CCTCACTGTT GATCGGCTTG CGCGGCACAT TCTCTGAGAA
6951 AGCCAAACAC GCGCGCAACA GCAACGCGGC GGCGTGGTCG GCAAAAACGC
7001 TATATCTAGA CCTGCTTCGG GACCCGGATC CGAAGAACTC CGATGAAGAC
7051 GAAGGCAATG AGTTCGGAAT CACTTACGGT CTCTCTTTCC ATGAACGCCG
7101 CCCGACCAGC AGCCACAGGC ACCACTGGTT CAAGGTGGGA TCGATACTGG
7151 ATTATCCTAC AGACGAGCAG CTGGAGGGGT TGATTGCCAA GGTGAAGACC
7201 GAATTTCATC ATGGTGTATC GGATTGGGAA AAGGGGCTGG CGGAAGACAC
7251 CCTGCGCCGG TTGCACCGCG TCATCTGGAA AGACGAGGGC ATCAACTTTT
7301 TCACTGAACG CGACCAGTCG GTTGATCGGG TGCTGGACAT CTTCGTGCGG
7351 GCCAATGACG GGGGCACGAA ACTGTCGAAG GCAGACCTGC TGATGTCGAT
7401 GATCACGTCA AAATGGTCCA GCGGATCGGC CCGCGAGGAA ATCGGCGGCT
7451 TTGTCGAGCA CATAAACAAA GGTCTCGGTG CGCCGAACAA GATCAGTCGC
7501 GATCTGGTCC TGAAGGCCTG TCTGGTCGTC TGCGATTATG ATGTCGTCTA
7551 TAATGTCAGG AACTTTACAA GCGAGGTCAT CGGCAGGATC GAAAGCAACT
7601 GGGATCGTAT CAAGCAGGCA TTCGAGAACA CGTTCCGCCT GCTGAACAGG
7651 CATGGCATCA CCGGGGATAA CCTCGGCTCT TTGAACGCGG TGCTGCCTCT
7701 GGTCTATTAT ATCTACAACA CGCCGGATTT CGATTTCCGA GGATCGAGCG
7751 AGTTCGAGCG GGTCAATGCC AGCTCCATGC ACCTCTGGTT GGTGAACAGC
7801 CTGCTGGTCA GCGCCTTCGT TGGCCATTCG GATCAGACCA TCACCACCGC
7851 GCGCAATACG ATCCGCGATC ACCTGCGTGT AGGCCGCGAT TTCCCAGTAC
7901 GAAAGCTGTT CGATGCCATG GCGAAGGGGG GACGGCTATC TCAGGTGGAT
7951 GAGCGTACCA TCGAAGAATT GCTGGAAATG CAATATGGCA AGCCCCGGAC
8001 CTTCGTTGCG CTGTCGCTGC TCTATCAGGG CATCGACTGG AACGGATCGA
8051 CCTGGCATGT CGATCATATC ATTCCCCAAG CGGACGCTCA GAAAAATGTG
8101 CTGCGCGGGC GCAATCTGCC CGAGCATCGC ATTCAGGAAA TCTTGGGCGC
8151 GGTTAACAGT TTGGGCAACC TGCAACTTTT GCGCGGAGAT GAGAATATCG
8201 AGAAAGGTGC GCTGCCATTC AGGTCATGGA TTACCGGACG GCGCGTTGAT
8251 TTCTACGAGC AGCATATGAT CCCGGCGCAC CTTGAACTGT GCGATGTACT
```

FIGURE 1D

```
8301  GCATCTGCCC GAGTTCGTGC GCGAACGGGA AAAGGTGATC CGGCGCCGTT
8351  TGATGGAGTT GGTCGGAGCA CGACGCGCAT GAATGAGGTC GTCTTGTCAC
8401  GCGAAGAGCT GCGTCAATCT TGTCTCGACC TGCTTGAAAA ACGCGCTGTC
8451  GAACACCCTG CGGGACACCA AGGCAAGCTC GCCGCCCGCT ATGTTGTGCA
8501  CCGCGACGA
```

FIGURE 1E

ENDOGENOUS KETOGULONIGENIUM PLASMID

CROSS-REFERENCE TO RELATED APPLICATIONS

This application claims the benefit of U.S. Provisional Application No. 60/194,625, filed Apr. 5, 2000, the content of which is incorporated herein by reference.

STATEMENT OF GOVERNMENT RIGHTS IN THE INVENTION

Part of the work performed during development of this invention utilized U.S. Government funds. The U.S. Government has certain rights in this invention.

BACKGROUND OF THE INVENTION

1. Field of the Invention

The present invention relates, in general, to an isolated or purified Ketogulonigenium plasmid endogenous to microorganism strain NRRL B-30035 (ADM 291-19).

2. Background Information

The exploitation of microorganisms to synthesize vitamin C or its chemical pathway intermediates has both economic and ecological advantages. One key intermediate in vitamin C synthesis is 2-keto-L-gulonic acid (2-KLG), which is easily converted chemically to L-ascorbic acid (vitamin C) by esterification followed by lactonization (Delic, V. et al., "Microbial reactions for the synthesis of vitamin C (L-ascorbic acid," in *Biotechnology of Vitamins, Pigments and Growth Factors*, Vandamme, E. J., ed., Elsevier Applied Science (London & New York) pp. 299–336 (1989)). Members of a number of bacterial genera have been identified that produce 2-KLG from the oxidation of L-sorbose. Such 2-KLG producing genera include the acidogenic, alpha-proteobacteria Gluconobacter and Acetobacter, the gamma-proteobacteria Pseudomonas, Escherichia, Klebsiella, Serratia and Xanthmonas, the Gram positive Bacillus, Micrococcus, and the unofficial genus Pseudogluconobacter (Imai, K. etal., U.S. Pat. No. 4,933,289 (1990), Sugisawa, H. et al., "Microbial production of 2-keto-L-gulonic acid from L-sorbose and D-sorbitol by *Gluconobacter melanogenus*," *Agric. Biol. Chem.* 54:1201–1209 (1990), Yin, G. et al., U.S. Pat. No. 4,935,359 (1990) and Nogami, I. et al., U.S. Pat. No. 5,474,924 (1995)).

To aid in increasing the yield of bacterial products, attempts have been made to exploit endogenous plasmids within microorganism strains. (Beppu, T. et al., U.S. Pat. No. 5,580,782 (1996), Fujiwara, A. et al., U.S. Pat. No. 5,399,496 (1995)).

SUMMARY OF THE INVENTION

One aspect of the invention provides an isolated or purified nucleic acid molecule comprising a polynucleotide having a nucleotide sequence at least 95% identical to a sequence selected from the group consisting of: a nucleotide sequence in SEQ ID NO: 1; a nucleotide sequence of an endogenous plasmid contained in NRRL Deposit No. B-30035; and a nucleotide sequence complementary to any of the above.

Further embodiments of the invention include isolated nucleic acid molecules that comprise a polynucleotide having a nucleotide sequence at least 90% identical, and more preferably at least 95%, 97%, 98% or 99% identical, to any of the above nucleotide sequences, or a polynucleotide which hybridizes under stringent hybridization conditions to a polynucleotide having a nucleotide sequence as in the above. The polynucleotide which hybridizes does not hybridize under stringent hybridization conditions to a polynucleotide having a nucleotide sequence consisting of only A residues or of only T residues.

Further advantages of the present invention will be clear from the description that follows.

BRIEF DESCRIPTION OF THE DRAWINGS

FIGS. 1A–1E shows the nucleotide (SEQ ID NO: 1) sequence of the endogenous plasmid determined by sequencing of the endogenous plasmid contained in NRRL Deposit No. B-30035. The nucleotide had a sequence of about 8509 nucleic acid residues.

DETAILED DESCRIPTION OF THE INVENTION

Unless otherwise indicated, all nucleotide sequences determined by sequencing a DNA molecule herein were determined using an automated DNA sequencer (such as the ABI Prism 3700). Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence in is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxynucleotide A, G or C of SEQ ID NO:1 has been replaced by the corresponding ribonucleotide A, G or C, and each deoxynucleotide T has been replaced by a ribonucleotide U.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

In another aspect, the invention provides an isolated nucleic acid molecule comprising a polynucleotide which hybridizes under stringent hybridization conditions to a portion of the polynucleotide in a nucleic acid molecule of the invention described above, for instance, in the endogenous plasmid contained in NRRL B-30035. By "stringent hybridization conditions" is intended overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 μg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers.

Of course, polynucleotides hybridizing to a larger portion of the reference polynucleotide (e.g., the deposited endogenous plasmid), for instance, a portion 50–750 nt in length, or even to the entire length of the reference polynucleotide, also useful as probes according to the present invention, as are polynucleotides corresponding to most, if not all, of the nucleotide sequence of the deposited DNA or the nucleotide sequence as shown in FIG. 1 (SEQ ID NO:1). By a portion of a polynucleotide of "at least 20 nt in length," for example, is intended 20 or more contiguous nucleotides from the nucleotide sequence of the reference polynucleotide, (e.g., the deposited DNA or the nucleotide sequence as shown in FIG. 1 (SEQ ID NO:1)). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual,* 2nd. edition, edited by Sambrook, J., Fritsch, E. F. and Maniatis, T., (1989), Cold Spring Harbor Laboratory Press, the entire disclosure of which is hereby incorporated herein by reference.

One aspect of the invention provides an isolated nucleic acid molecule comprising a polynucleotide having a nucleotide sequence at least 95% identical to a sequence selected from the group consisting of: (a) a nucleotide sequence in SEQ ID NO:1; (b) a nucleotide sequence of an endogenous plasmid contained in NRRL Deposit No. B-30035; and (c) a nucleotide sequence complementary to any of the nucleotide sequences in (a) or (b) above.

Further embodiments of the invention include isolated nucleic acid molecules that comprise a polynucleotide having a nucleotide sequence at least 90% identical, and more preferably at least 95%, 97%, 98% or 99% identical, to any of the nucleotide sequences in (a), (b) or (c) above, or a polynucleotide which hybridizes under stringent hybridization conditions to a polynucleotide having a nucleotide sequence identical to a nucleotide sequence in (a), (b) or (c), above. The polynucleotide which hybridizes does not hybridize under stringent hybridization conditions to a polynucleotide having a nucleotide sequence consisting of only A residues or of only T residues.

By a polynucleotide having a nucleotide sequence at least, for example, 95% "identical" to a reference nucleotide sequence is intended that the nucleotide sequence of the polynucleotide is identical to the reference sequence except that the polynucleotide sequence may include up to five point mutations per each 100 nucleotides of the reference nucleotide sequence encoding the pyruvate carboxylase polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

As a practical matter, whether any particular nucleic acid molecule is at least 90%, 95%, 97%, 98% or 99% identical to, for instance, the nucleotide sequence shown in FIG. 1 (SEQ ID NO: 1) or to the nucleotide sequence of the deposited endogenous plasmid can be determined conventionally using known computer programs such as the FastA program. FastA does a Pearson and Lipman search for similarity between a query sequence and a group of sequences of the same type nucleic acid. Professor William Pearson of the University of Virginia Department of Biochemistry wrote the FASTA program family (FastA, TFastA, FastX, TFastX and SSearch). In collaboration with Dr. Pearson, the programs were modified and documented for distribution with GCG Version 6.1 by Mary Schultz and Irv Edelman, and for Versions 8 through 10 by Sue Olson.

The present application is directed to nucleic acid molecules at least 90%, 95%, 97%, 98% or 99% identical to the nucleic acid sequence shown in FIG. 1 (SEQ ID NO:1) or to the nucleic acid sequence of the deposited endogenous plasmid.

A Ketogulonigenium strain harboring an endogenous plasmid DNA was deposited under the terms of the Budapest Treaty on Jun. 18, 1998, at the Agricultural Research Service Culture Collection (1815 North University Street, Peoria, Ill. 61604 U.S.A.) and given the NRRL-Deposit No. B-30035. The present invention relates to an isolated or purified nucleic acid molecule comprising a nucleotide sequence of an endogenous plasmid contained in NRRL Deposit No. B-30035.

The molecule of the present invention is suitable for use as a vector. As such, polynucleotides of interest can be joined to the nucleic acid molecule of the present invention, which may optionally contain a selectable marker.

The vector can optionally contain an exogenous terminator of transcription; an exogenous promoter; and a discrete series of restriction endonuclease recognition sites, said series being between said promoter and said terminator. The vector can optionally contain its native expression vector and/or expression vectors which include chromosomal-, and episomal-derived vectors, e.g., vectors derived from bacterial exogenous plasmids, bacteriophage, and vectors derived from combinations thereof, such as cosmids and phagemids.

A DNA insert of interest should be operatively linked to an appropriate promoter, such as its native promoter or a host-derived promoter, the phage lambda $P_L$ promoter, the phage lambda $P_R$ promoter, the *E. coli lac* promoters, such as the lacI and lacZ promoters, trp and tac promoters, the T3 and T7 promoters and the gpt promoter to name a few. Other suitable promoters will be known to the skilled artisan.

The expression constructs will further contain sites for transcription initiation, termination and, in the transcribed region, a ribosome binding site for translation. The coding portion of the mature transcripts expressed by the constructs can include a translation initiating codon at the beginning and a termination codon appropriately positioned at the end of the polypeptide to be translated.

As indicated, the expression vectors will preferably include at least one marker capable of being selected or screened for. Preferably the selectable marker comprises a nucleotide sequence which confers antibiotic resistance in a host cell population. Such markers include amikacin, augmentin (amoxicillin plus clavulonic acid), ampicillin, cefazolin, cefoxitin, ceftazidime, ceftiofur, cephalothin, enrofloxacin, florfenicol, gentamicin, imipenem, kanamycin, penicillin, sarafloxicin, spectinomycin, streptomycin, tetracycline, ticarcillin, tilmicosin, or chloramphenicol resistance genes. Other suitable markers will be readily apparent to the skilled artisan.

Methods used and described herein are well known in the art and are more particularly described, for example, in J. H. Miller, *Experiments in Molecular Genetics*, Cold Spring Harbor Laboratory Press, Cold Spring Harbor, N.Y. (1972); J. H. Miller, *A Short Course in Bacterial Genetics*, Cold Spring Harbor Laboratory Press, Cold Spring Harbor, N.Y. (1992); M. Singer and P. Berg, *Genes & Genomes*, University Science Books, Mill Valley, Calif. (1991); J. Sambrook, E. F. Fritsch and T. Maniatis, *Molecular Cloning: A Laboratory Manual*, 2d ed., Cold Spring Harbor Laboratory Press, Cold Spring Harbor, N.Y. (1989); P. B. Kaufman et al., *Handbook of Molecular and Cellular Methods in Biology and Medicine*, CRC Press, Boca Raton, Fla. (1995); *Methods in Plant Molecular Biology and Biotechnology*, B. R. Glick and J. E. Thompson, eds., CRC Press, Boca Raton, Fla. (1993); P. F. Smith-Keary, *Molecular Genetics of Escherichia coli*, The Guilford Press, New York, N.Y. (1989); *Plasmids: A Practical Approach*, 2nd Edition, Hardy, K. D., ed., Oxford University Press, New York, N.Y. (1993); *Vectors: Essential Data*, Gacesa, P., and Ramji, D. P., eds., John Wiley & Sons Pub., New York, N.Y. (1994); *Guide to Electroporation and electrofusions*, Chang, D., et al., eds., Academic Press, San Diego, Calif. (1992); *Promiscuous Plasmids of Gram-Negative Bacteria*, Thomas, C. M., ed., Academic Press, London (1989); *The Biology of Plasmids*, Summers, D. K., Blackwell Science, Cambridge, Mass. (1996); *Understanding DNA and Gene Cloning: A Guide for the Curious*, Drlica, K., ed., John Wiley and Sons Pub., New York, N.Y. (1997); *Vectors: A Survey of Molecular Cloning Vectors and Their Uses*, Rodriguez, R. L., et al., eds., Butterworth, Boston, Mass. (1988); *Bacterial Conjugation*, Clewell, D. B., ed., Plenum Press, New York, N.Y. (1993); Del Solar, G., et al., "Replication and control of circular bacterial plasmids," *Microbiol. Mol. Biol. Rev.* 62:434–464 (1998); Meijer, W. J., et al., "Rolling-circle plasmids from Bacillus subtilis: complete nucleotide sequences and analyses of genes of pTA1015, pTA1040, pTA1050 and pTA1060, and comparisons with related plasmids from gram-positive bacteria," *FEMS Microbiol. Rev.* 21:337–368 (1998); Khan, S. A., "Rolling-circle replication of bacterial plasmids," *Microbiol. Mol. Biol. Rev.* 61:442–455 (1997); Baker, R. L., "Protein expression using ubiquitin fusion and cleavage," *Curr. Opin. Biotechnol.* 7:541–546 (1996); Makrides, S. C., "Strategies for achieving high-level expression of genes in *Escherichia coli*," *Microbiol. Rev.* 60:512–538 (1996); Alonso, J. C., et al., "Site-specific recombination in gram-positive theta-replicating plasmids," *FEMS Microbiol. Lett.* 142:1–10 (1996); Miroux, B., et al., "Over-production of protein in *Escherichia coli*: mutant hosts that allow synthesis of some membrane protein and globular protein at high levels," *J. Mol. Biol.* 260:289–298 (1996); Kurland, C. G., and Dong, H., "Bacterial growth inhibited by overproduction of protein," *Mol. Microbiol.* 21:1–4 (1996); Saki, H., and Komano, T., "DNA replication of IncQ broad-host-range plasmids in gram-negative bacteria," *Biosci. Biotechnol. Biochem.* 60:377–382 (1996); Deb, J. K., and Nath, N., "Plasmids of corynebacteria," *FEMS Microbiol. Lett.* 175:11–20 (1999); Smith, G. P., "Filamentous phages as cloning vectors," *Biotechnol.* 10:61–83 (1988); Espinosa, M., et al., "Plasmid rolling cicle replication and its control," *FEMS Microbiol. Lett.* 130:111–120 (1995); Lanka, E., and Wilkins, B. M., "DNA processing reaction in bacterial conjugation," *Ann. Rev. Biochem.* 64:141–169 (!995); Dreiseikelmann, B., "Translocation of DNA across bacterial membranes," *Microbiol. Rev.* 58:293–316 (1994); Nordstrom, K., and Wagner, E. G., "Kinetic aspects of control of plasmid replication by antisense RNA," *Trends Biochem. Sci.* 19:294–300 (1994); Frost, L. S., et al., "Analysis of the sequence gene products of the transfer region of the F sex factor," *Microbiol. Rev.* 58:162–210 (1994); Drury, L., "Transformation of bacteria by electroporation," *Methods Mol. Biol.* 58:249–256 (1996); Dower, W. J., "Electroporation of bacteria: a general approach to genetic transformation," *Genet. Eng.* 12:275–295 (1990); Na, S., et al., "The factors affecting transformation efficiency of coryneform bacteria by electroporation," *Chin. J. Biotechnol.* 11:193–198 (1995); Pansegrau, W., "Covalent association of the traI gene product of plasmid RP4 with the 5'-terminal nucleotide at the relaxation nick site," *J. Biol. Chem.* 265:10637–10644 (1990); and Bailey, J. E., "Host-vector interactions in *Escherichia coli*," *Adv. Biochem. Eng. Biotechnol.* 48:29–52 (1993).

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference.

EXAMPLES

Example 1

DNA Preparation

Ketogulonigenium cells (NRRL No. B-30035 (ADM 291-19)) harvested from Trypticase Soy Broth (TSB, Difco) cultures were suspended in 10 ml of TE pH 8 (10 mM Tris·Cl, 1 mM EDTA) containing 0.5% sodium dodecyl sulfate (SDS) and 0.1 mg/l proteinase K and lysed by incubation at 37° C. for one hour. Nucleic acids were purified by three extractions with TE-saturated phenol (pH7), three TE-saturated phenol/chloroform/isoamyl alcohol (25:24:1), and two chloroform extractions followed by ethanol precipitation. Nucleic acid precipitates were twice washed with 80% ethanol and redissolved in TE pH 8. Chromosomal and plasmid DNAs were separated by centrifugation in CsCl gradients. The existence of an extra chromosomal band in the EtBr-CsCl DNA-purification gradient suggested the presence of at least one plasmid.

After harvesting the DNA bands from the gradients, excess ethidium bromide was removed by repeated water-saturated butanol and the final DNA preparations purified using Centricon 30 columns (Amicon) as per manufacturer's recommendations. The concentrations of DNA were quantified spectrophotometrically at 260 nm. Purity of DNA preparations were determined spectrophotometrically ($A_{260}/A_{280}$ and $A_{260}/A_{230}$ ratios) and by agarose gel electrophoresis (0.8% agarose in 1×TAE). A single plasmid was identified from strain ADM 291–19 (pADM291) of about 8 kb.

pADM291 was sequenced by walking primers. A Sau3AI digest was done on pADM291 and ligated into the BamHI site of pUC19. The forward primer generated a sequence and primer walking on the pADM291 plasmid generated all the other sequences.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

---

What is claimed is:

1. An isolated or purified nucleic acid molecule comprising a polynucleotide having a nucleotide sequence at least 95% identical to a sequence selected from the group consisting of:
   (a) a nucleotide sequence in SEQ ID NO:1;
   (b) a nucleotide sequence of an endogenous plasmid contained in NRRL Deposit No. B-30035; and
   (c) a nucleotide sequence complementary to any of the nucleotide sequences in (a) or (b).

2. The nucleic acid molecule of claim 1 wherein said polynucleotide has the complete nucleotide sequence in SEQ ID NO:1.

3. An isolated nucleic acid molecule comprising a polynucleotide which hybridizes under stringent hybridization conditions to a polynucleotide having a nucleotide sequence identical to a nucleotide sequence in (a), (b) or (c) of claim 1 wherein said polynucleotide which hybridizes does not hybridize under stringent hybridization conditions to a polynucleotide having a nucleotide sequence consisting of only A residues or of only T residues.

4. A vector comprising the isolated nucleic acid molecule of claim 1, and at least one marker gene.

5. A vector comprising:
  (a) the nucleic acid molecule of claim 1;
  (b) a terminator of transcription;
  (c) a promoter; and
  (d) a discrete series of restriction endonuclease recognition sites, said series being between said promoter and said terminator.

6. The vector of claim 4, wherein said marker gene comprises a nucleotide sequence operative to direct synthesis of a protein conferring antibiotic resistance in a host cell population.

7. The vector of claim 6, wherein said antibiotic is selected from the group consisting of ampicillin, chloramphenicol, erythromycin, kanamycin, spectinomycin, streptomycin and tetracycline.

8. An isolated or purified vector, said vector comprising a DNA sequence that is at least 95% identical to a sequence selected from the group consisting of:
  (a) SEQ ID NO:1;
  (b) the sequence of the endogenous Ketogulonigenium plasmid that is contained in NRRL Deposit No. B-30035 and that hybridizes under stringent conditions to a plasmid having the sequence of SEQ ID NO:1;
  (c) a nucleotide sequence that is complementary to a nucleotide sequence of part (a) or (b).

9. The isolated or purified vector of claim 8, wherein said nucleotide sequence is at least 95% identical to that of part (a).

10. The isolated or purified vector of claim 8, wherein said nucleotide sequence is at least 95% identical to that of part (b).

11. The isolated or purified vector of claim 8, wherein said nucleotide sequence is at least 95% identical to that of part (c).

12. The isolated or purified vector of claim 9, wherein said nucleotide sequence is that of part (a).

13. The isolated or purified vector of claim 10, wherein said nucleotide sequence is that of part (b).

14. The isolated or purified vector of claim 11, wherein said nucleotide sequence is that of part (c).

15. The vector of any one of claims 8–14, wherein said vector further comprises a marker gene.

16. The vector of any one of claims 8–14, wherein said vector further comprises a DNA insert of interest.

17. The vector of any one of claims 8–14, wherein said vector further comprises a discrete series of restriction endonuclease recognition sites.

18. A Ketogulonigenium host cell that has been transformed with the vector of any one of claims 8–14.

19. The vector of claim 15, wherein said marker gene comprises a nucleotide sequence that is operative to direct synthesis of a protein that confers antibiotic resistance in a host cell population.

20. The vector of claim 19, wherein said antibiotic resistance is selected from the group consisting of ampicillin resistance, chloramphenicol resistance, erythromycin resistance, kanamycin resistance, spectinomycin resistance, steptomycin resistance and tetracycline resistance.

21. A Ketogulonigenium host cell that has been transformed with the vector of claim 15.

22. A Ketogulonigenium host cell that has been transformed with the vector of claim 19.

23. A Ketogulonigenium host cell that has been transformed with the vector of claim 20.

24. A Ketogulonigenium host cell that has been transformed with the vector of claim 16.

25. A Ketogulonigenium host cell that has been transformed with the vector of claim 17.

* * * * *

SEQUENCE LISTING

<160> NUMBER OF SEQ ID NOS: 1

<210> SEQ ID NO 1
<211> LENGTH: 8509
<212> TYPE: DNA
<213> ORGANISM: Ketogulonigenium

<400> SEQUENCE: 1

| | | | | | |
|---|---|---|---|---|---|
| tggtgaacgc | attggcttga | tgtttgagaa | aagcgaaaag | acccggccac | agttgtgggt | 60 |
| agagcgtcga | tatgtgcaag | acctgatgct | tgctgacatc | gaactccgtg | tctacctcgc | 120 |
| atcgtcgctg | tatcagcctg | ctgcggatgg | cggaaagccc | gcctatggtc | gtcacgcagc | 180 |
| ccttaaggcg | atgcgcgact | tggcccatgc | cgatctggtc | cgtttcacca | tcggccggat | 240 |
| tacgcaactg | gagatgatcc | tagagcggtt | aaccgagaca | tctggttaac | gccataaagg | 300 |
| ctgcggcatg | aaaataggcg | gacaatctgc | gcttggccgc | ccccgttctc | agccgtgctt | 360 |
| gctctctgcc | tgcatggcac | gacgcaggat | cgcgttcata | cgggtctgat | atccagaccc | 420 |
| gcccgccttg | agccatgcca | gcacatcggc | atcaagccgc | gcggtgatct | gctgcttgat | 480 |
| cgggcgatag | aagcgcccac | gctcggcgtc | tgcccattgg | gcttcggtca | gctcgggaac | 540 |
| atcgttggtg | tcgatctgct | cgggcggcag | agcgtccagc | cgcgccaatt | tcttgcggcg | 600 |
| ctcctcggta | agagcgggca | gcgtatcgaa | ggtgtattca | accattggca | tatctcttcc | 660 |
| tttcctgcgg | tgtagcgcgg | cgagccgaaa | tgatgcggat | cgtctcgacc | ggatcggggc | 720 |
| cagcctcgat | gatcaggtgg | gcaaccagaa | ggacggcagc | gccatagatc | tgcccaacgg | 780 |
| tttgccagcg | gtattccccg | ccctcgatcc | tatcctgaac | cgtcaggtgc | aacggatcgg | 840 |
| cgaacacatg | cacagcatcc | tcgaaccgga | tgccatgctt | cttttcgttc | gtttccgcct | 900 |
| tggcgggatc | ccagataaac | cgcatcttca | tggcagaatt | ataactacac | atttgtagtt | 960 |
| attcaatggc | aagtcgcagg | ttcaaatcac | gcccccaaac | cgcaactgta | ttcgttctac | 1020 |
| tcacgcgcgc | ttttgaatag | aagcttgcat | gataacaccc | gccgcgtcct | caacaaaata | 1080 |
| aggcaaatcc | gccgcgctgg | cgcaatctgc | gctttgtcga | tgcaaggtct | tgtggtttca | 1140 |
| tactgcaaga | gcatgcaagg | aattgccccg | gatgagcacc | acgacgacac | ccaccaagcc | 1200 |
| ggcctggaac | aagggccgcg | ttgtcgggaa | aaagccgccg | ctgacacctg | accagattgc | 1260 |
| cctgatccgt | ctcatcctgc | gccaggaacg | ggcgtggcgg | gatctggctc | tgttcaacgt | 1320 |
| ggcgatcgac | accagtttgc | gcggctcgga | cctcgtgcgc | ctgcgcgtct | cggatgtggc | 1380 |
| gaccccagct | ggtctgcgtg | agatcgtcga | gatccgccag | aagaagaccg | aggcccgcaa | 1440 |
| tgtccgcccc | gtacaggccc | gcctgtcgga | ggggacacgc | gagagcctgc | gggtctatct | 1500 |
| cgcggcctct | gacaagccgc | tgcacagctg | gctgttcacc | ggacagggca | tccgctggtc | 1560 |
| ccacacccac | cttagcgaga | gccagctgtg | gcgcctgttc | aagtcctggc | tcgagaaggc | 1620 |
| gcggctcgat | cccagcctct | acgggctgca | ctcgctgcgc | cgaaccttcc | ccagccacat | 1680 |
| ctaccgcgag | accggcaatc | tgcgcgccgc | acagctgctg | ctgggccatg | ccagcatcga | 1740 |

-continued

```
gagcaccaag gagtacatcg gcaccgagca agccgaggcc ctcgatatcg cacggaggta      1800
tcacctctaa cccatggaga cctatctcga aagcgcatc cccgccaaga acacagcacg       1860
gttctaccgc atggcggtcc tgccgaacct gttcggggaa tggacgctgt atcgagaatg     1920
gggccgcatt ggcatcagcg gccgcatccg gctcgattgg tttgagagtg aacaagatgc    1980
catcgctgcg atgctcgcca tcgagaccgc caagcgtcag cgcgggtatt ggctcgagcc     2040
catccagatt gacatgttcc caggggcata acaggccatc aatgtaagag tgcaagcgga    2100
gcaagcaaaa gccatttcac agtgaggtgg cagatgttcc tgtttcacag tgaaagcgct     2160
gatgctgttt ccacgccaca gactgatacg accaaagcaa cggggtctgc cgccacagac   2220
cggttcgccg gccacccgca gaaacgcagg taaaatggca atttccgcaa aaaaccgtg      2280 caaatgatgg caaatcacca tccagtttca tcctgaaacc cgtcgctcaa catgaacgag   2340
caggccatca tccaagcccc agaaacgcgg tgcggcgact acagatgagc gatgttctgg    2400
ctcataggct gcaaggccct gcaacagtga tttcaccgtg agattgcagg gtcttttggc      2460
tctcccgcaa gagccacctc agggtgagcg agctagccgt ctaggttcac agtgaaatcg   2520
ctgaggagcg ttgcggggct tatggtttgg ctggtcacgt tggccatcgg aatggagcat   2580
acgatggctt ctacgcagtc gaatcctgag gcttcacgtg ggaaaaatac gctccaaaaa    2640
agccctgacc aaatcttgga aaaattgctt gaaaagtttg cttctaaaaa actgggaacg    2700
agatatgcac gagatccctt acgagtgctg taggagtaat gcagtggaca aaaacgccat     2760
tttttgcccc agtaggagta atggagtggt tattttttgg gagattttgc ttcagtagga    2820
gtaacgcgtt ggttaaattt gcttgattgg cggttcaaat cgaccaccga gctgccgttg    2880
gtcgtattcg atctgccccg caattgggca cttgcaggcc atcccctga acttctggcg    2940 atgaccattt cgaaggcaat gggtcgaaat tcatagaatt ttgtgtgagg tgcgtagcgg    3000
ctctgacagg ggtgctgcgc ggagatctct ggtctcaggt agggcgacaa tggagaggtg    3060
ttagttgccc cctgtatcgc tctctgcgtg gcgcattggg tcatcctgcc cggacatatg    3120
atattccgct agaggattac tgatagtttc tgcctgtcgg gcttgtcggg cttgtcgggc    3180
ttgtcgggct tgtcgggcct gtccctcttg tcccgcctgt cctcactttt tcacaatcaa    3240
aaaatgggcg aagcccttct tgttctatag ttcttatagt tcatacgaaa attacacata    3300
attatcaata gcttattcgc ttaaaaggga gtaattgggc cgcaaaaggg agtaattggg    3360
ccgcaaaagg gagtaattgg gccgcaaaag ggagtaattg ggccgatatc ggttgtttac    3420
atggggagga atcccttaa tcatttctcc ccatgggaaa acaacacaa gtggccgcag     3480 accgggcctt cgaccagaca aaaactgtgc tccctgccga ggtggcgaga ggggtctata   3540
tgcgcaatcc gccccgcctg caggcgctca agctcatgca tttaatgata gccactgcgg    3600
gcggccgcat ggctgatgat gtgcgccatg aaatgcggct ggccgacatt cgcgcaatcg   3660
acggcatgaa aaccatgac cgtgagagcc tgaccccgct gttcgaggag ctagccgctg    3720
cggtgttgac ccatgatgac cctgcaaaga tgatcgtgac agtcggcggc ttggtcgatg    3780
aggcgcgaat agactaccgc caggaggcaa gcggcgaact cctagtgacg tggaccttcc    3840
ggagtacatt ccgtcgtatg gcggcggagt cgaaccactg gccattctc gaccgtcaaa     3900 cggtattcca tctcggtagt aagtattccg tgctgctgtt ccagcacgtc tctagtctcg   3960
ccaatcttga tcggatgagc gcgaaaacct ttacggtccc cgagttgcgg gcgctccttg    4020
gagtgcccga ggaaagatg gttcgttgga acgacgttaa cagatttgct ctcaaacctg    4080
```

-continued

```
cactggatga gatcaaccat ttatcgcgtc tgacattgac ggcaaagccg accaagattg    4140
gccgtagcgt ggcaagtgtg actataggct gggaagtgaa agacgaccca accgtcgcca    4200
ggcgcgagct ggcgggttcc aaggtcggtc gagatgctcg tcgcagaggg gcagcggaaa    4260
cgatagcccc ctccttccca gaagcgggcg ggatcaccta cagtccacgt tggctggagc    4320
tgaaacgctc tgctggcagc aacaaggaca acgatctgat cgcctcagac ttccggcgtt    4380
tctgtcggga gagaggcgtg cgtctggacg ctgcaaacat cgaaaaactg tttttagatt    4440
tctgcgcaaa ggtagggaag gtttgagttt tgaggtattt caccgcaata gtgttaaatg    4500
actttcgtga aacgatgtgc aatatagcgg taagactatg aaatacacgg ctggacaggc    4560
tgcaaaagca acgggtgtgg cgaccgcaac catcactcgg gcgctaaaaa gcggtaaaat    4620
ttccggtaaa aaagatgaat ctggggcatg ggttatagat cctgcagaat tgcacagagt    4680
gtttcctccc atttcaaaga aatacaccga aacacctaac acgcaagtat atggtaagcg    4740
tgatgaaaca catgaaatga cctcagaaat cagcgcatta gagcgtgaag ttcggacttt    4800
acgcgatgct ttatctgatg ccagggagga tcgcgacaaa tggcgcgaca tggccgagcg    4860
tctttcaatt tcatcaccga tgagagagga agaccgcccc cctcaaaaac aaagatggtg    4920
gaagatattc tgatcctggg cttcaggagc cttgccttta aaacctgaat cagcattcta    4980
gcgatgctga taagaagtaa atatagccac aatagagcgg ccattttcca ttcacataca    5040
gctcatcatg tgatcaatat caagtattga tattcatcaa tggagaagaa tttacatgta    5100
tcacaggatc atcacagcat ttgttttttgt atttctaagt gctaacataa ctatcgctgg    5160
ccctaaagaa gattgtacta ttgcagtatc tcaccttggg tttcagaccg ataattacag    5220
ctttgtcgaa gccggttttt tgccagaga gagacacgtt tttgatggtg taataaactg    5280
ctacgtatct catgatggta acatacacag catcatccgg ggcaacacac ctcttatgga    5340
agatggatat tatggcccag aagtactggc ggaaaaacgc gatattgagg cacaggcccg    5400
cactttagag gcggaagcct ataacgagta ccaaaacact agaagccaga ttgaggaaaa    5460
tagggaacgt gccctcgagg cgctgcggct agctagcagt cctttttatta ataatggtag    5520
tacagaagaa cagacaatta tacaggccgc aactccgacg gcagatcctg ttgtatctgt    5580
acccgtggca tctccagaat ctaaacaaag tcgagagccg gaaccggctg ctgttccagc    5640
atcagtttct gttagagaga tgtggagcac ggctgacaga ttgaccaccc gtacatgccc    5700
atcgactcga tgcggagcaa ctagctgggt aacagatgga actaaagtaa cagtttatga    5760
agaaaaagac ggttggtcta aatcggaga gctacagtct gcaatgtgca taaatggaat    5820
aagtggcgcg tcgattcag gtgaatcttc ctgcaatccc accaatggta tcgttaatgg    5880
gcaattcgca ccctgggttt tctcggatta tcttacgatc caagagccag aagctcccat    5940
atccacccaa gagtgtcgaa atatggggct cgagaactca gataattacc gtatctattc    6000
tagtcagttc tgcactgccg ctctcgaaat gatcaacgat agagtatgca atacatctga    6060
tttcagagat ttagcttggt tatcttctcc tgaaagagga caggattact acttcaccta    6120
ttgtggcgga tttcaacctc aaaacagatg gtatttgaat gtcaggacag gtgaaatcac    6180
ccgctgatat tccaccaagg tgagtcctgt agatcagact ctcaaggagt aaacgtttta    6240
atccatctcc atgagatcaa catagatagg tgttcagtcc cggcatctgg tggatcgggt    6300
ttaggatgaa tctgtccggc tcttgacata ccccgcgtg aaaccctgtc tttacaagag    6360
aaagtcagcg gcctcgaagc cgctctagcc gatgcccggg cccaacggga tgagtagagc    6420
gaacaagcaa agcgcctagc tatggctctg cccgtcccgg aagctgcagc cgcagaatcc    6480
```

```
ggaaaaaaga aaaaatacat ggcagcgatt atttggatag gacacaatcc ttttctatta    6540
atatacaaca agatatgggc atgcgccgcg cgtgatcctc attcgataca atccaaatcc    6600
tgaaagctga ctatgcccta cgcatcgcgc accatcggtg ccgtcattga tgacgtgaac    6660
cgcacctacc tgctgcccgc aatccaacgc ccctatgtct ggtctgccgg acaggtcgtt    6720
gcgctgttcg actctctgtt gaagggctat ccgatcagca gcttcatgtt ctgggcggtg    6780
gacgaggaga ccaaggcaga gctgcgatgc tacaaattca tcgagaatta tcggcccgaa    6840
atgatgaacg agccgactag tgcggacggg cggcaggtcg tccttgtgct cgacggacag    6900
cagcggatga cctcactgtt gatcggcttg cgcggcacat tctctgagaa agccaaacac    6960
gcgcgcaaca gcaacgcggc ggcgtggtcg gcaaaaacgc tatatctaga cctgcttcgg    7020
gacccggatc cgaagaactc cgatgaagac gaaggcaatg agttcggaat cacttacggt    7080
ctctctttcc atgaacgccg cccgaccagc agccacaggc accactggtt caaggtggga    7140
tcgatactgg attatcctac agacgagcag ctggagggt tgattgccaa ggtgaagacc    7200
gaatttcatc atggtgtatc ggattgggaa aagggggctgg cggaagacac cctgcgccgg    7260
ttgcaccgcg tcatctggaa agacgagggc atcaactttt tcactgaacg cgaccagtcg    7320
gttgatcggg tgctggacat cttcgtgcgg gccaatgacg ggggcacgaa actgtcgaag    7380
gcagacctgc tgatgtcgat gatcacgtca aaatggtcca gcggatcggc ccgcgaggaa    7440
atcggcggct ttgtcgagca cataaacaaa ggtctcggtg cgccgaacaa gatcagtcgc    7500
gatctggtcc tgaaggcctg tctggtcgtc tgcgattatg atgtcgtcta taatgtcagg    7560
aactttacaa gcgaggtcat cggcaggatc gaaagcaact gggatcgtat caagcaggca    7620
ttcgagaaca cgttccgcct gctgaacagg catggcatca ccggggataa cctcggctct    7680
ttgaacgcgg tgctgcctct ggtctattat atctacaaca cgccggattt cgatttccga    7740
ggatcgagcg agttcgagcg ggtcaatgcc agctccatgc acctctggtt ggtgaacagc    7800
ctgctggtca gcgccttcgt tggccattcg gatcagacca tcaccaccgc gcgcaatacg    7860
atccgcgatc acctgcgtgt aggccgcgat ttcccagtac gaaagctgtt cgatgccatg    7920 gcgaagggg gacggctatc tcaggtggat gagcgtacca tcgaagaatt gctggaaatg    7980
caatatggca agccccggac cttcgttgcg ctgtcgctgc tctatcaggg catcgactgg    8040
aacggatcga cctggcatgt cgatcatatc attccccaag cggacgctca gaaaaatgtg    8100
ctgcgcgggc gcaatctgcc cgagcatcgc attcaggaaa tcttgggcgc ggttaacagt    8160
ttgggcaacc tgcaacttt gcgcggagat gagaatatcg agaaaggtgc gctgccattc    8220
aggtcatgga ttaccggacg gcgcgttgat ttctacgagc agcatatgat cccggcgcac    8280
cttgaactgt gcgatgtact gcatctgccc gagttcgtgc gcgaacggga aaaggtgatc    8340
cggcgccgtt tgatggagtt ggtcggagca cgacgcgcat gaatgaggtc gtcttgtcac    8400
gcgaagagct gcgtcaatct tgtctcgacc tgcttgaaaa acgcgctgtc gaacaccctg    8460
cgggacacca aggcaagctc gccgcccgct atgttgtgca ccgcgacga                8509
```